US008518428B2

(12) United States Patent
Shen et al.

(10) Patent No.: US 8,518,428 B2
(45) Date of Patent: Aug. 27, 2013

(54) ANTAGONISTIC BACTERIA FOR CONTROLLING THE *FUSARIUM* WILT OF CONTINUOUS CROPPING BANANA AND THEIR MICROBIAL ORGANIC FERTILIZER

(75) Inventors: Qirong Shen, Nanjing (CN); Xin He, Nanjing (CN); Qiwei Huang, Nanjing (CN); Xingming Yang, Nanjing (CN); Biao Shen, Nanjing (CN)

(73) Assignees: Nanjing Agricultural University, Jiangsu (CN); Jiangsu New Ground Bio-Fertilizer Engineering Center Co., Ltd, Jiangsu (CN)

( * ) Notice: Subject to any disclaimer, the term of this patent is extended or adjusted under 35 U.S.C. 154(b) by 338 days.

(21) Appl. No.: 12/747,500

(22) PCT Filed: Nov. 17, 2009

(86) PCT No.: PCT/CN2009/074973
§ 371 (c)(1),
(2), (4) Date: Jun. 10, 2010

(87) PCT Pub. No.: WO2011/032329
PCT Pub. Date: Mar. 24, 2011

(65) Prior Publication Data
US 2011/0214463 A1 Sep. 8, 2011

(30) Foreign Application Priority Data
Sep. 18, 2009 (CN) .......................... 2009 1 0183361

(51) Int. Cl.
*A01N 25/08* (2006.01)
(52) U.S. Cl.
USPC ..................... 424/409; 424/76.6; 424/93.462; 424/115; 424/405; 424/406; 435/252.5; 435/839; 71/6; 71/8; 71/10; 71/12; 71/21; 71/35

(58) Field of Classification Search
USPC .................. 71/6, 8, 10, 12, 21, 35; 424/76.6, 424/93.462, 115, 123, 406, 409; 435/252.5
See application file for complete search history.

(56) References Cited

U.S. PATENT DOCUMENTS
7,442,224 B2 * 10/2008 Porubcan ............................ 71/6

FOREIGN PATENT DOCUMENTS
CN 1415737 A 5/2003
CN 1590535 A 3/2005
(Continued)

OTHER PUBLICATIONS
Abstract 2009:97536 DOC. # 150;167402—HCAPLUS—Guo et al—CN 101348389.*
(Continued)

*Primary Examiner* — Neil Levy
(74) *Attorney, Agent, or Firm* — Knobbe, Martens, Olson & Bear, LLP

(57) ABSTRACT

The present invention relates to the antagonistic bacteria for controlling the *Fusarium* wilt of continuous cropping banana and their microbial organic fertilizer. It belongs to technology of intensive agricultural production. The present invention separates two antagonistic bacteria NJN-6 and NJN-11 and produces the microbial organic fertilizer through inoculating the two said strains into pig manure compost and rapeseed cake compost to conduct solid-state fermentation. The microbial organic fertilizer is characterized in that in the fertilizer, the content of each of the antagonistic bacteria NJN-6 and NJN-11 is above $1 \times 10^8$ cfu/g, total nitrogen is 4~5% (weight percent), above 90% (weight percent) of the total nitrogen is organic nitrogen, total nitrogen-phosphorus-kalium nutrient is 6~10% (weight percent) and organic matter is 30~35% (weight percent). The results of experiment showed the showed that the prevention rate of the *Fusarium* wilt of banana reached more than 80% and the incidence rate can be controlled to less than 5% even on the seriously diseased terraces (seasonal incidence rate of 15% or more). The fertilizer can control the wilt effectively if they are applied to soil in successive years.

5 Claims, 2 Drawing Sheets

(56) References Cited

FOREIGN PATENT DOCUMENTS

| CN | 1236051 C | 1/2006 |
|---|---|---|
| CN | 101186887 A | 5/2008 |
| CN | 101250495 A | 8/2008 |
| CN | 100500005 C | 6/2009 |
| CN | 101485336 A | 7/2009 |
| CN | 101503659 A | 8/2009 |
| CN | 101575574 A | 11/2009 |
| JP | 9002911 A | 1/1997 |

OTHER PUBLICATIONS

Sun et al., "Antagonistic Rhizobacteria Strain *Bacillus subtilis* S 1 Against Banana Fusarium Wilt", Chinese Journal of Biological Control, 24(2)143-147 (May 2008).

Nel et al., "The Potential of Nonpathogenic Fusarium Oxysporum and Other Biological Control Organisms for Suppressing Fusarium Wilt of Banana", Plant Pathology, 55:217-223 (2006).

International Search Report issued in International application No. PCT/CN/2009/074973 on Mar. 24, 2011.

International Search Report issued in International application No. PCT/CN2009/075076 on Jul. 15, 2010.

International Search Report issued in International application No. PCT/CN2009/074977 on Mar. 24, 2011.

Lin et al., "Test on the Control Efficacy of Antagonistic Microorganism on Watermelon Wilt Disease" Journal of Guangxi Agric. and Biol. Science, 21(4):242-244 (Dec. 2002).

Zhu et al., "Effect of Biocontrol Strain Anti-8098A of *Bacillus cereus* on Pathogenicity of Ralstonia Solanacearum", Chinese journal of biological control, 25(1):41-47 (2009).

Yi et al., "Isolation and Identification of Endophytic Brevibacillus Brevis and its Biocontrol Effect Against Tobacco Bacterial Wilt", Acta Phytopathologica Sinica, 37(3):301-306 (2007).

Ramesh et al., "Pseudomonads: Major Antagonistic Endophytic Bacteria to Suppress Bacterial Wilt Pathogen, Ralstonia Solanacearum in the Eggplant (*Solanum melongena* L.)", World J. Microbiol Biotechnol., 25:47-55 (2009).

\* cited by examiner ical Solution

ANTAGONISTIC BACTERIA FOR CONTROLLING THE *FUSARIUM* WILT OF CONTINUOUS CROPPING BANANA AND THEIR MICROBIAL ORGANIC FERTILIZER

BACKGROUND OF THE INVENTION

1. Field of the Invention

The present invention relates to the antagonistic bacteria for controlling the *Fusarium* wilt of continuous cropping banana and their microbial organic fertilizer. It belongs to technology of intensive agricultural production.

2. Description of the Related Art

Since the *Fusarium* wilt of continuous cropping banana was first found in China in 2001, the soil-borne disease has spread rapidly. Currently the situation is getting worse in main banana production areas in China including Hainan Province, Guangdong Province, Guangxi Zhuang Autonomous Region. So far the disease has impacted banana production seriously. *Fusarium* wilt of continuous cropping banana is caused by pathogenic fungi (*Fusarium oxysporum* f. sp. Cubense Race 4), which occurs at the time of the fourth cutting, and grew more seriously after the sixth cutting. If there is no methods or ways to control the disease, it will be difficult to produce banana in the next five to ten years, which will have a significant impact on the banana industry and people's lives in China. The result of our research suggested that the key issue of *Fusarium* wilt of the continuous cropping crops is neither lack or imbalance of nutrients, nor is the problem of soil secondary salinization, but is the problem with soil microbial flora and its secondary material toxicity.

On the other hand, the straw of paddy, wheat, corn, rape and other crops are burned on the spot and the excrement of the livestock and poultry raised on a scale is discarded. It not only seriously pollutes environment but also is a great waste of the raw material that can be used to produce organic fertilizer and bio-organic fertilizer products; enormous nutritive resources (C, N, P, K, S and trace elements) are lost outside the soil-plant system and the sustainable development of Chinese agriculture is obviously weakened. How to maximally return the nutritive elements taken away from soil due to harvesting of crops to the soil? The only way is to make these solid organic wastes into commercial organic fertilizer and apply the fertilizer into the soil. If these solid organic wastes are synthesized into high-grade organic compost through high-temperature fermentation and then the compost is used as a carrier of functional bacteria to prepare microbial organic fertilizer, the function will be clear and there will be a good application prospect.

SUMMARY OF THE INVENTION

Technical Problem

The purpose of the present invention is to provide the antagonistic bacteria for controlling the *Fusarium* wilt of continuous cropping banana and their microbial organic fertilizer. It can control the wilt effectively and increase the production. It can biologically restore the soil with continuous cropping obstacle and ensure the smooth development of intensive agriculture.

Technical Solution

The antagonistic bacteria for controlling the *Fusarium* wilt of continuous cropping banana include strain NJN-6 and strain NJN-11, both of which belong to *Bacillus subtilis* and have been collected in China General Microbiological Culture Collection Center (CGMCC) with their corresponding collection numbers are CGMCC No. 3183 and CGMCC NO. 3184.

The main biological characteristics of the Strain NJN-6 are as follows: Gram-positive; rod-shaped; terminal spore; facultative anaerobe; catalase-positive; oxidase-negative; V.P. reaction is positive; methyl red test is negative; the fermentation of glucose generates acid without gas; the fermentation of fructose generates acid and gas; xylose, L-arabinose and mannit can't be fermented; citrate-positive; nitratase-positive; amylase-positive; gelatin hydrolysis-positive; decompose reaction of casein is positive.

The main biological characteristics of the Strain NJN-11 are Gram-positive; rod-shaped; terminal spore; facultative anaerobe; catalase-positive; oxidase-negative; V.P. reaction is positive; methyl red test is positive; the fermentation of glucose and fructose generates acid without gas; xylose, L-arabinose and mannit can't be fermentated; citrate-positive; nitratase-positive; amylase-positive; gelatin hydrolysis-positive; decompose reaction of casein is positive.

The microbial organic fertilizer that is produced from the above-mentioned antagonistic bacteria for controlling the *Fusarium* wilt of continuous cropping banana is characterized in that in the fertilizer, the content of each of the antagonistic bacteria NJN-6 and NJN-11 is above $1 \times 10^8$ cfu/g, total nitrogen is 4~5% (weight percent), above 90% (weight percent) of the total nitrogen is organic nitrogen, total nitrogen-phosphorus-kalium nutrient is 6~10% (weight percent) and organic matter is 3~035% (weight percent).

The said microbial organic fertilizer is produced by following methods, wherein:

(1) Said antagonist bacteria NJN-6 and NJN-11 respectively conducts liquid fermentation production under the following conditions: the culture solution is potato-dextrose-agar (PDA), with the pH value at 6.0~7.0 and the culture temperature is 30~35° C.; the speed of stirring is 180~300 r/min; fermentation time is 48 hours; the amount of bacteria or spores in fermentation broth $\geq 1 \times 10^{10}$ ind/mL; preparation methods of PDA culture solution (taking the preparation of 1 L culture medium as an example) are as follows: unpeel 200 g potato, cut it into small dices, and boil it in boiling water for 30 min, and subsequently filter the mixture with a four-layered medical gauze, add 20 g of common sucrose into the filtrate, fix the volume at 1000 mL, adjust pH value to 7.2-7.4, and sterilize the liquor at 121° C. for 20 min.

(2) The NJN-6 and NJN-11 fermentation liquor are respectively incubated to mature pig excrement compost and the mixture from microbial enzymatic hydrolysis of rapeseed meal at a dosage of 50 L/t. to conduct solid fermentation. The fermentation temperature is lower than 50° C. During the fermentation, the material is turned over once a day. The fermentation is completed in five days to ensure the content of antagonistic bacteria is above $1 \times 10^8$ cfu/g. In the end, the solid microbial agents of antagonist NJN-6 and NJN-11 are obtained; the germination index of the mature pig excrement compost is more than 98%, the content of organic matter is $\geq 35\%$, the content of organic nitrogen is 1.2-2% and water content is 25-30%.

(3) By two types—compost and the mixture from microbial decomposition of rapeseed meal, antagonist NJN-6 solid microbial agents and antagonist NJN-11 solid microbial agents are mixed at a volume ratio of 1:1 to obtain the mixed solid microbial agents of compost and the mixed solid microbial agents of the mixture from microbial decomposition of rapeseed meal.

(4) The mixed solid microbial agents of compost (50-70% v/v) and the mixed solid microbial agents of the mixture from microbial enzymatic hydrolysis of rapeseed meal (30-50% v/v) are thoroughly mixed. The mixture is ripened for 2-3 days. During the ripening, it is turned over twice. In the end, the microbial organic fertilizer is evaporated at temperature of not above 60° C. till its water content is less than 30%. After packaging, the microbial organic fertilizer that controls the *Fusarium* wilt of continuous cropping banana is obtained.

The microbial organic fertilizer can be exclusively used to control the *Fusarium* wilt of continuous cropping banana . . .

Beneficial Effects

The advantages of the present invention compared to the other organic fertilizer products on the market are as follows:

1) The fertilizer products contain high efficient strain NJN-6 and NJN-11 which can inhibit the growth of pathogenic fungi of *Fusarium* wilt of banana. The inhibition effect is very remarkable. The experimental results showed that the prevention rate of the *Fusarium* wilt of banana reached more than 80% and the incidence rate can be controlled to less than 5% even on the seriously diseased terraces (seasonal incidence rate of 15% or more) (Table 2). The fertilizer can control the wilt effectively if they are applied to soil in successive years.

2) The fertilizer is organic fertilizer and contains rich organic matter (30-35%) and organic nitrogen (4%), mostly of which is amino acids and micromolecule peptides. The content of total phosphorus in the product is 4%. Moreover, the product has brilliant bioavailability. After the product is used, crops can successfully get through phosphorin sensitive period in seedling stage.

3) As it is a biological strain preparation, it doesn't have any problem caused by the use of chemical pesticides and is conducive to the pollution-free production of vegetables. Farmers may not use or reduce the dosage of other chemical pesticides that control the wilt. This not only can reduce farmers' expenditure but also can improve the quality of agricultural products. Meanwhile, the microbial fertilizer has the function of increasing yield, so farmers' revenue can be increased.

4) The microbial organic fertilizer can be used in nutrition pot and fields. They not only have the functions of organic fertilizer and also can control the banana Panama wilt through a variety of bio-control mechanism of the antagonistic bacteria.

DETAILED DESCRIPTION OF THE PREFERRED EMBODIMENT (I) Separation of Antagonistic Strains Primary screening of antagonistic strains: Acquisition of healthy banana rhizosphere soil in banana continuous cropping fields, using the combination of PDA and NA (nutrient agar) in which spores suspension of pathogen *Fusarium oxysporum* Race 4 (from China Collection Center for General Microbiology Culture) has been added to conduct double layer plate of screening antagonistic strains. Eleven antagonistic strains were obtained in the primary screening and were freeze-dried to be saved at −20° C. for further screening.

Figure 1:
FIG. 1 Antagonistic effect of NJN-6 strains
FIG. 2 Antagonistic effect of NJN-11 strains
FIG. 3. Antagonistic effect of NJN-6 strains in pots
(Note: T1: Control; T3: Organic Fertilizer Containing Njn-6)
FIG. 4. Antagonistic effects of NJN-11 strains in pots
(Note: T1: Control; T4: Organic Fertilizer Containing Njn-11)
FIG. 5 Antagonistic effect of mixed fertilizers containing strains NJN-6 and strains NJN-11 in pots
(Note: T1 control; T5: organic fertilizer containing both NJN-6 and NJN-11)
Figure 2:
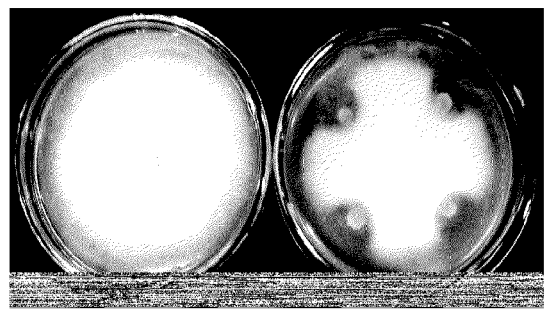

Secondary screening of antagonistic strains: The antagonist strains from the primary screening and pathogenic bacteria were collected for secondary screening by using confront culture on PDA plate. Get pathogen piece from the plate with punch (5 mm) and put it on the middle of the PDA plate for 24 h, and then inoculate the antagonist strains for test in the middle of PDA plate which is at a distance of 2 cm form pathogenic bacteria by sterile toothpicks, and subsequently put them into the incubator at 28° C. for 3~5 days. Obtain bacterial strain NJN-6 and NJN-11 by observation of the inhibition of antagonist bacteria colonies against pathogenic. Antagonistic effect of NJN-6 strain and NJN-11 strain were shown in FIG. 1 and FIG. 2.

(II) Identification of Antagonistic Strains

NJN-6 and NJN-11 strains were identified as *Bacillus subtilis*.

The main biological characteristics of the Strain NJN-6 are as follows: Gram-positive; rod-shaped; terminal spore; facultative anaerobe; catalase-positive; oxidase-negative; V.P. reaction is positive; methyl red test is negative; the fermentation of glucose generates acid without gas; the fermentation of fructose generates acid and gas; xylose, L-arabinose and mannit can't be fermentated; citrate-positive; nitratase-positive; amylase-positive; gelatin hydrolys is positive; decompose reaction of casein is positive.

The main biological characteristics of the Strain NJN-11 are as follows: Gram-positive; rod-shaped; terminal spore; facultative anaerobe; catalase-positive; oxidase-negative; V.P. reaction is positive; methyl red test is positive; the fermentation of glucose and fructose generates acid without gas; xylose, L-arabinose and mannit can't be fermentation; citrate positive; nitratase positive; amylase positive; gelatin hydrolysis positive; decompose reaction of casein is positive.

(III) Production of Microbial Agents (1) Antagonistic bacteria NJN-6 and NJN-11 are respectively inoculated to PDA culture solution for liquid fermentation. The fermentation conditions are as follows: the pH value is at 6.0~7.0 and the culture temperature is 24~37° C.; the speed of stirring is 180~300 r/min; fermentation time is 48 h; the amount of bacteria or spores in fermentation broth is $\geq 1\times10^{10}$ ind/mL; preparation methods of PDA culture solution (taking the preparation of 1 L culture medium as an example): Unpeel 200 g potato, cut it into small dices, and boil it in boiling water for 30 min, then filter the mixture with a four-layered medical gauze, adding 20 g of common sucrose into the filtrate, fix the volume at 1000 mL, adjust pH value to 7.2-7.4, and sterilize the liquor at 121° C. for 20 min.

(2) The NJN-6 and NJN-11 fermentation liquors are respectively incubated to mature pig excrement compost and the mixture from microbial enzymatic hydrolysis of rapeseed meal at a dosage of 50 L/t. to conduct solid fermentation. The fermentation temperature is lower than 50° C. During the fermentation, the material is turned over once a day. The fermentation is completed in five days to ensure the content of antagonistic bacteria is above $1\times10^8$ cfu/g. In the end, the solid microbial agent of antagonist NJN-6 and NJN-11 are obtained; the germination index of the mature pig excrement compost is more than 98%, the content of organic matter is $\geqq 35\%$, the content of organic nitrogen is 1.2-2% and water content is 25-30%.

The mixture from microbial decomposition of rapeseed meal is produced by the following method (known and used by the public, see Chinese patent of invention ZL200610086 126.0, a biological preparation method of amino acids for agricultural use and their fertilizer product): add the fermentation liquor of strain 37-1 into raw material rapeseed meal; adjust water content to 55-65% and pH value to 6.0-7.5; conduct open solid fermentation; turn it over once the fermentation temperature rises to 50° C.; turn it over every day since then, and maintain the temperature at 35-50° C. for 5 days. After solid fermentation starts, the pH value of the material will keep rising. Whenever it is turned over, acidic liquid should be added to adjust water content and pH value and maintain water content at 55-65% and pH value at 6.0-7.0. When the fermentation is terminated, acidic liquid will be sprayed again till pH value of the material is about 5.0. After that, the material is dried at low temperature or air. The final product is the mixture from microbial decomposition of rapeseed meal (mixture containing amino acids).

(3) By two types—compost and the mixture from microbial decomposition of rapeseed meal, antagonist NJN-6 solid microbial agent and antagonist NJN-11 solid microbial agent are mixed at a volume ratio of 1:1 to obtain the mixed solid microbial agent of compost and the mixed solid microbial agent of the mixture from microbial decomposition of rapeseed meal.

(4) The mixed solid microbial agent of compost (70% v/v) and the mixed solid preparation of the mixture from microbial enzymatic hydrolysis of rapeseed meal (30% v/v) are thoroughly mixed. The mixture is ripened for 2-3 days. During the ripening, it is turned over twice. In the end, the microbial organic fertilizer is evaporated at temperature of not above 60° C. till its water content is less than 30%. The single-strain microbial organic fertilizer (including NJN-6 and NJN-11 respectively) and mixture microbial organic fertilizer (including both of NJN-6 and NJN-11) that controls the *Fusarium* wilt of continuous cropping banana are obtained.

The mixture microbial organic fertilizer (the microbial organic fertilizer can be exclusively used to control the *Fusarium* wilt of continuous cropping banana) is characterized in that in the fertilizer, the content of each of the antagonistic bacteria NJN-6 and NJN-11 is above $1\times10^8$ cfu/g, total nitrogen is 4~5% (weight percent), above 90% (weight percent) of the total nitrogen is organic nitrogen, total nitrogen-phosphorus-kalium nutrient is 6~10% (weight percent) and organic matter is 30~35% (weight percent).

(IV) Control Effect Experiment in Greenhouse

The experiment sets up four treatments: T1—control, without application of micro-organic fertilizer; T3—application of single-strain microbial organic fertilizers (including NJN-6 strains); T4—application of single-strain microbial organic fertilizers (including NJN-11 strains); T5—application of complex microbial organic fertilizer (including both NJN-6 strains and NJN-11 strains). The amount of microbial organic fertilizer: application in weight of 2% of soil when seedling (healthy soil is used when seedling) and transplanting to banana continuous cropping soil when the 5th ture leaf appeared. All the amount of nitrogen-phosphorus-kalium is processed uniformly and managed regularly. To observe the incidence, the morbidity is recorded to confirm whether it can inhibit the *Fusarium* wilt of banana.

Figure 3:
Figure 4:
Figure 4:
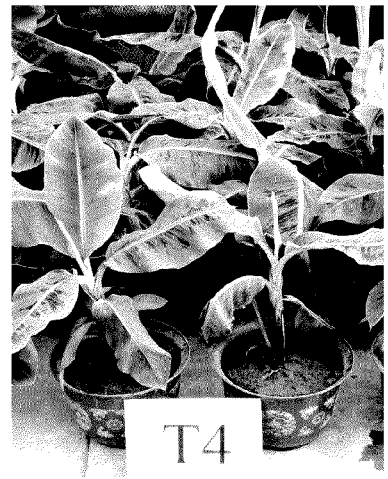
Figure 5:
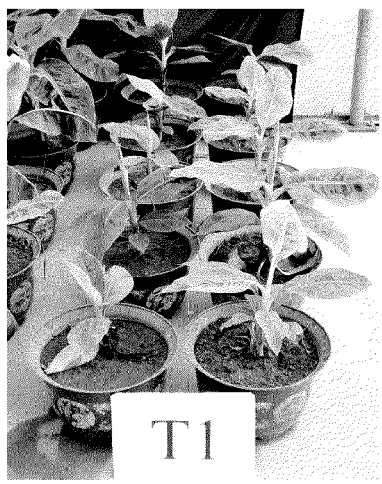
Figure 5:
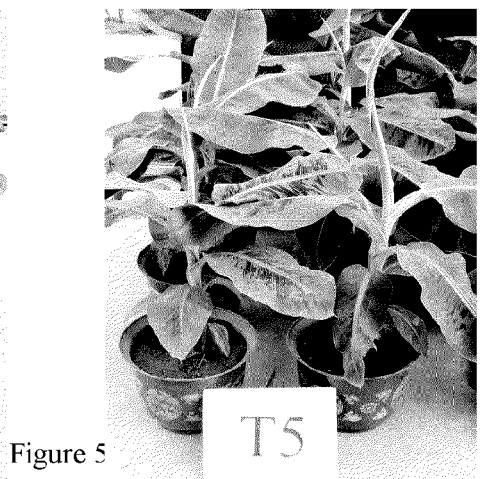

Thirty days after transplanting the banana seedling, diseased plant is found in T1 (control, without application of micro-organic fertilizer), and in another 20 days, 80% of the plants is diseased in T1, while the variety incidence of situations exist in other handlings in the meantime. The control rate and morbidity of plants in 50 days after transplanting were shown in Table 1. The result of pot experiment showed that the control rates of *Fusarium* wilt of banana were 75% and 68% by using organic fertilizer containing NJN-6 (T3) and NJN-11 (T4) respectively (FIG. 3, FIG. 4), wherein T5—application of complex micro-organic fertilizer (with both NJN-6 strains and NJN-11 strain) has the best effects and a control rate up to 87.5% (FIG. 5).

TABLE 1

Effects of different microbial organic fertilizer for controlling banana Panama wilt

| Treatment | T1 | T3 | T4 | T5 |
|---|---|---|---|---|
| Morbidity | 80% | 20% | 25% | 10% |
| The rate of disease prevention | / | 75% | 68.8% | 87.5% |

TABLE 2

Impaction of different microbial organic fertilizer on banana Panama wilt of soil microbial flora

| Treatment | bacteria (cfu/g of soil) | Actinomycosis (cfu/g of soil) | fungus (cfu/g of soil) |
|---|---|---|---|
| T1 | $1.54 \times 10^8$ | $3.57 \times 10^6$ | $2.3 \times 10^5$ |
| T3 | $1.49 \times 10^9$ | $6.8 \times 10^7$ | $2.4 \times 10^4$ |
| T4 | $2.56 \times 10^9$ | $2.87 \times 10^7$ | $6.9 \times 10^4$ |
| T5 | $2.87 \times 10^9$ | $4.33 \times 10^7$ | $3.1 \times 10^4$ |

Note:
T1: CK (fertilizer); T3: single-strain microbial organic fertilizer containing specific antagonistic bacteria against Fusarium wilt of banana (NJN-6); T4: single-strain microbial organic fertilizer containing specific antagonistic bacteria against Fusarium wilt of banana (NJN-11); T5: mixed microbial organic fertilizer containing both NJN-6 and NJN-11 strains; all the soils for test are banana continuous cropping soils.

(V) Field Experiment

Apply a special microbial organic fertilizer for controlling *Fusarium* wilt of banana in nutritional bowl seeding and fields at the same time. The amount of microbial organic fertilizer is as follows: 1.5% in weight when transplanting in nutrition pot, and 1.5 kg per tree as application rate when transplanting in fields (amount to 225 kg/mu). The results showed that the *Fusarium* wilt of banana could be controlled in less than 5% in severe wilt fields (seasonal morbidity of 15% or more) (Table 3). In accordance with the price of 8 yuan per kilogram of bananas, application of microbial organic fertilizer in nutritional bowl seeding and fields at the same time will increase income by 3424 yuan/mu for the farmer. After deducting 517.5 yuan/mu as the cost of the microbial organic fertilizer, the banana farmers have a net gain of 2906.5 yuan/mu, which make large-scale application of organic fertilizers become possible.

TABLE 3

Effects of applicating microbial organic fertilizer on controlling Fusarium wilt of banana

| Treatment | Morbidity of Fusarium wilt (%) | Yield of banana (Kg/mu) | Increasing rate (%) |
|---|---|---|---|
| Control (with application of microbial organic fertilizers in nutrition pot and transplanting) | 18 ± 2.3 | 2505 ± 85 | — |
| Application of microbila organic fertilizers in nutrition pot | 7.8 ± 1.8 | 3127 ± 94 | 24.8 |
| Application of microbial organic fertilizers in fields | 12.1 ± 2.1 | 2989 ± 74 | 19.3 |
| Application of microbial organic fertilizers in both nutrition pot and fields | 4.5 ± 1.5 | 3361 ± 88 | 34.2 |

Note:
The amount of microbial organic fertilizer is as follows: 1.5% in weight when transplanting in nutrition pot, and 1.5 kg per tree as application rate when transplanting in fields (amount to 225 kg/mu)

The present invention proceeds from the key issue of microbial flora (Table 2), and develops a microbial organic fertilizer product to eliminate the *Fusarium* wilt of banana significantly with bio-control rate of 80% or more. The mechanism of the fertilizer products lies in effective carbon and nitrogen sources in fertilizer products which provide good conditions for the effective functional bacteria cultivation of microbial flora such that establishes ecology and the food chain of exogenous beneficial functional bacteria microbial rapidly; on the other hand, the fertilizer product contains a high content of organic nitrogen and phosphorus which is very beneficial to the growth of the banana in the soil with continuous cropping obstacle and can greatly enhance the banana seedling-standing ratio and anti-adversity ability as well.

What is claimed is:

1. A microbial organic fertilizer for controlling *Fusarium* wilt in continuous cropping bananas comprising:

antagonistic bacteria wherein said antagonistic bacteria comprise *Bacillus subtilis* strain NJN-6 and *Bacillus subtilis* strain NJN-11, both of which are deposited under identification numbers CGMCC 3183 and 3184, respectively, and a content of each of *Bacillus subtilis* strain NJN-6 and *Bacillus subtilis* strain NJN-11 is above $1\times10^8$ colony-forming unit (cfu) per 1 gram of the fertilizer; and nitrogen with an amount of 4~5% weight percent of a total weight of the fertilizer, wherein above 90% weight percent of a total weight of said nitrogen is organic nitrogen, and 6~10% weight percent of the total weight of said nitrogen is nitrogen-phosphorus-kalium;

wherein a portion of organic matter in the fertilizer is 30~35% weight percent of the total weight of the fertilizer.

2. A method of producing the microbial organic fertilizer according to claim 1, comprising:

inoculating each of the antagonist bacteria strains NJN-6 and NJN-11 into two different PDA culture media, respectively and conducting liquid fermentation wherein the liquid fermentation condition is as follows: a pH value is at 6.0~7.0; a culture temperature is 30~35° C.; a speed of stirring is 180~300 r/min; fermentation time is 48 h; a quantity of bacteria or spores of each of said antagonist bacteria strains in its respective fermentation broth is about $1\times10^{10}$ colony-forming unit (cfu) per 1 ml of the fermentation broth;

inoculating part of the fermentation broth comprising the antagonist bacteria strain NJN-6 into mature pig excrement compost and incubating another part of the fermentation broth comprising the antagonist bacteria strain NJN-6 into a mixture from microbial enzymatic hydrolysis of rapeseed meal at a dosage of 50 L/t; and inoculating part of the fermentation broth comprising the antagonist bacteria strain NJN-11 into mature pig excrement compost and incubating another part of the fermentation broth comprising the antagonist bacteria strain NJN-11 into a mixture from microbial enzymatic hydrolysis of rapeseed meal at a dosage of 50 L/t, wherein all of the four foregoing incubations undergo solid fermentation under the following conditions: a fermentation temperature for the solid fermentation is lower than 50° C.; during the solid fermentation, materials present in each of the incubations are turned over once a day; the solid fermentation is completed in 5 days to ensure a content of their respective antagonistic bacteria strain is above $1\times10^8$ cfu per 1 gram of the fertilizer; thereby providing the following four solid microbial agents:

a first solid microbial agent comprising the antagonistic bacteria strain NJN-6 and the mature pig excrement compost;

a second solid microbial agent comprising the antagonistic bacteria strain NJN-6 and the mixture from microbial enzymatic hydrolysis of rapeseed meal;

a third solid microbial agent comprising the antagonistic bacteria strain NJN-11 and the mature pig excrement compost;

a fourth solid microbial agent comprise the antagonistic bacteria strain NJN-11 and the mixture from microbial enzymatic hydrolysis of rapeseed meal;

mixing the first solid microbial agent and the third solid microbial agent at a volume ratio of 1:1 to provide a first mixed solid microbial agent and mixing the second solid microbial agent and the fourth solid microbial agent at a volume ratio of 1:1 to provide a second mixed microbial agent;

thoroughly mixing the first mixed solid microbial agent (50 to 70% v/v) and the second mixed solid microbial agent (30 to 50% v/v); and ripening a resulting mixture comprising the first mixed solid microbial agent and the second mixed solid microbial agent for 2 to 3 days wherein during the ripening the resulting mixture is turned over twice, and undergoes evaporation at temperature of not above 60° C. till a water content of the resulting mixture is less than 30%.

3. The method according to claim 2, wherein the PDA culture media are prepared by the following method:
per 1 liter of the PDA culture media,
unpeeling 200 g potato;
cutting the unpeeled potato into small dices;
boiling the potato dices in water for 30 min;
filtering the boiled potato dices to provide a filtrate;
adding 20 g common sucrose into the filtrate;
fixing a volume of a mixture comprising the filtrate and the common sucrose at 1000 mL to provide a mixture liquor;
adjusting a pH value of the mixture liquor to 7.2-7.4; and
sterilizing the mixture liquor at 121° C. for 20 min.

4. The method according to claim 2, wherein in the mature pig excrement compost a germination index of the mature pig excrement compost is more than 98%, a content of organic matter is ≧equal to or above 35% weight percent of a total weight of the mature pig excrement compost, and a content of organic nitrogen is 1.2-2% weight percent and a water content is 25-30% weight percent of the total weight of the mature pig excrement compost, respectively.

5. A method of controlling *Fusarium* wilt in continuous cropping bananas comprising:
applying the microbial organic fertilizer according to claim 1 to an area that is in need of such controlling.

* * * * *